United States Patent [19]

Lewis, Jr. et al.

[11] 4,097,473
[45] Jun. 27, 1978

[54] PRODUCTION OF SERUM ALBUMIN

[75] Inventors: Charles Lewis, Jr., Hazelwood; James M. Schuck, Chesterfield, both of Mo.

[73] Assignee: Monsanto Company, St. Louis, Mo.

[21] Appl. No.: 828,013

[22] Filed: Aug. 26, 1977

Related U.S. Application Data

[63] Continuation of Ser. No. 707,906, Jul. 22, 1976, abandoned.

[51] Int. Cl.$^2$ .............................................. C07G 7/00
[52] U.S. Cl. ................................ 260/122; 260/112 B; 424/101; 424/177
[58] Field of Search ............................ 260/112 B, 122

[56] References Cited

U.S. PATENT DOCUMENTS

| | | | |
|---|---|---|---|
| 2,469,193 | 5/1949 | Cohn | 260/112 B |
| 2,705,230 | 3/1955 | Reid | 260/112 B X |
| 2,765,299 | 10/1956 | Porsche et al. | 260/112 B |
| 2,958,628 | 1/1960 | Hink | 260/112 B X |
| 3,100,737 | 8/1963 | Auerswald | 260/112 B X |
| 3,554,985 | 1/1971 | Fields et al. | 260/78 X |
| 3,555,001 | 1/1971 | Wallis et al. | 260/122 X |

OTHER PUBLICATIONS

*Blut*, Band 30, Seite 121–134 (1975), Schneider et al.
*Laboratory Techniques in Biochemistry & Mol. Biology*, vol. 2 pp. 344, 345, Work et al.
*Biochem. Biophysica Acta.* vol. 82:221 (1964) Stockwell et al.
*Chromatographic and Electrophoretic Methods* 3rd Ed. pp. 476 & 406, Heftman, (1975).
*Separation Methods in Biochemistry*, 2nd Ed. pp. 320, 321 & 350, Morris et al. (1976).

*Primary Examiner*—Howard E. Schain
*Attorney, Agent, or Firm*—Scott J. Meyer; John D. Upham

[57] ABSTRACT

A serum albumin fraction is prepared in high yield and purity from plasma and other albumin-containing blood protein fractions by contacting with a resinous polymeric material having a high capacity for adsorption of albumin, heating at 65° C–72° C for about 1–4 hours while maintaining a pH of 5.0–5.5, and then selectively eluting the albumin from the resin-protein mixture at a pH of 3.5–4.5. The resinous polymeric materials are water-insoluble, cross-linked polyelectrolyte copolymers of ethylene and maleic anhydride containing pendant dimethylaminopropyl functional groups.

13 Claims, No Drawings

PRODUCTION OF SERUM ALBUMIN

This is a continuation of application Ser. No. 707,906, filed July 22, 1976, now abandoned.

BACKGROUND OF THE INVENTION

This invention relates to blood fractions and more particularly to a method for the preparation of a serum albumin fraction in high yield and purity.

Albumin constitutes the largest fraction of blood plasma and finds wide use in medical therapy such as in cases of shock and as a plasma extender.

The fractionation of blood by various procedures to obtain albumin and recover other separated components is an established practice. A principal albumin fraction of commerce known as normal serum albumin is an osmotically stable solution of a highly purified plasma fraction containing at least 96% albumin. Its availability has been made possible largely through the work of Cohn and his associates at the Harvard Medical School and its preparation is described in U.S. Pat. Nos. 2,390,074 and 2,469,193; *J. Amer. Chem. Soc.* 68, 469–75 (1946); Kirk-Othmer, *Encyl. of Chem Tech.*, 3, 584–88 (2d. ed. 1964'). The current method of choice in the United States for the preparation of normal serum albumin is the so-called Method 6 of Cohn.

Another principal albumin fraction of commerce is the so-called plasma protein fraction (PPF) which is a solution of a plasma fraction containing at least 83% albumin together with a mixture of not more than 17% α -and β - globulins. The current method of choice in the United States for the production of PPF is that of Hink as described in U.S. Pat. No. 2,958,628 and *Vox Sang*, 2, 174 (1957).

The foregoing procedures for obtaining the more highly concentrated normal serum albumin and the less concentrated PPF make use of cold etnanol as a precipitating agent in the fractionation schemes. Various other known procedures for the preparation of albumin fractions make use of other precipitating agents such as ether, methanol or ammonium sulfate salt, or involve adsorption on gels or ion exchange chromatography.

More recently, various polymeric materials have been developed for the fractionation of blood, including the separation of albumin, for example, polyethylene glycol (PEG, Carbowax) as described in U.S. Pat. No. 3,415,804; copolymers of ethylene oxide and polyoxypropylene polymer (Pluronics) as disclosed in U.S. Pat. No. 3,850,903 and German Offenlegunsschrift No. 2,403,065; and certain unique polyelectrolytes such as ethylene/maleic anhydride, cross-linked copolymer derivatives defined in U.S. Pat. Nos. 3,554,985 and 3,555,001. An advantage of the use of these polymeric materials is that they can be employed at normal room temperature and thus avoid the cold temperature requirements of the Cohn ethanol fractionation procedure. While the various polymeric fractionation methods are useful for preparation of PPF, they have not, in general, provided the optimum yield and purity of the normal serum albumin fraction as obtained by the cold ethanol procedure.

Still another method of obtaining a purified serum albumin involves the selective denaturation of serum globulins without denaturation of the serum albumin by heating in the presence of caprylate or other fatty acid anion stabilizers as described in U.S. Pat. Nos. 2,705,230 and 2,765,299; *J. Biol. Chem.* 162, 181–98 (1948); and *Blut* 30, 121–134 (1975). While useful for the preparation of PPF type albumin fractions, this method is not generally suitable for the preparation of the more highly purified normal serum albumin in high yields without destruction of valuable gamma globulins. It is usually carried out as a pasteurization step to provide a virus-free albumin product.

BRIEF SUMMARY OF THE INVENTION

In accordance with the present invention a serum albumin fraction is prepared in high yield and purity from plasma and other albumin-containing blood fractions by contacting with a resinous polymeric material having high capacity for adsorption of albumin, heating at a temperature of from about 65° C to about 72° C for about one to about 4 hours while maintaining a pH of from about 5.0 to about 5.5, and then selectively eluting the albumin from the resin-protein mass at a pH of from about 3.5 to about 4.5. The resinous polymeric materials employed in this invention are water-insoluble, cross-linked polyelectrolyte copolymers of ethylene and maleic anhydride containing pendant dimethylaminopropyl functional groups. The combination of the heat treatment and the adsorption-elution steps with these polyelectrolyte copolymers provides an albumin product in substantially higher purity and yield than obtained separately with either the heat treatment step or the adsorption-elution steps.

DETAILED DESCRIPTION OF THE INVENTION

The serum albumin prepared in accordance with this invention can be obtained from whole blood, blood plasma and serum, or fractions thereof known to contain albumin. Since the treatment with heat as employed herein tends to denature the globulins present in the treated material, it is frequently useful to first isolate certain desired globulin fractions, such as the gamma globulins, before proceeding with the method of the invention. Other valuable blood fractions such as the clotting factors, AHF and prothrombin complex, also can be initially separated from the plasma starting materials before proceeding with the method of the invention. These fractions can be separated by conventional procedures known in the art.

The water-insoluble, cross-linked polyelectrolyte copolymers employed in this invention are copolymers of ethylene and maleic anhydride containing pendant dimethylaminopropyl functional groups. The base copolymer of ethylene and maleic anhydride (EMA) can be prepared, for example, by reacting ethylene and maleic anhydride in the presence of a peroxide catalyst in a suitable solvent. The copolymer will preferably contain substantially equimolar quantities of the ethylene residue and the anhydride residue. The EMA copolymer can then be reacted with methyliminobispropylamine which has two primary amine groups and leads to a cross-linked EMA copolymer. The desired pendant dimethylaminopropyl functional groups can then be incorporated into the cross-linked copolymer by reaction of dimethylaminopropylamine with anhydride groups of the EMA copolymer. The polyelectrolyte copolymer also desirably is converted to the HCl salt form to provide better handling characteristics. Further details on the preparation and structure of these polyelectrolyte copolymers can be had by reference to the disclosure in U.S. Pat. No. 3,554,985. Use of these polyelectrolyte copolymers in blood fractionation is described in U.S. Pat. No. 3,555,001.

A preferred polyelectrolyte copolymer for use in this invention contains about five methyliminobispropylamine cross-linking groups and about 90 pendant dimethylaminopropylamine functional groups for 100 maleic anhydride units in the EMA copolymer.

Unexpectedly, it has been found that the foregoing polyelectrolyte copolymers have a high capacity for adsorption of albumin relative to certain other polyelectrolyte copolymers having different pendant amine functional groups. Thus, the polyelectrolyte copolymer defined herein is able to substantially completely adsorb all the albumin in the blood fraction which is then recoverable in greater than 90% yield and 94% purity following the heat treatment and selective elution. By way of comparison, a similar polyelectrolyte copolymer having, instead, 2-(aminoethyl)-1-ethylpyrrolidine pendant groups adsorbed only about 22% albumin and, of the material adsorbed, subsequent elution after heat treatment resulted in a product with a purity of only about 67%. Another similar polyelectrolyte copolymer having, instead, pendant 3-(di-n-butylamino)-propylamine groups adsorbed a major portion of the albumin, but after heat treatment none of the albumin could be eluted.

In carrying out the method of this invention, the foregoing polyelectrolyte copolymers are admixed with blood plasma or serum, or albumin-containing blood fractions, preferably at a concentration ranging from about 1% to about 5% copolymer. By adjusting the pH of the resin-protein mixture to varying levels, selected proteins can first be removed. At pH of about 5.5 to 7.5, albumin, $\alpha$ and $\beta$ globulins and fibrinogen are adsorbed by the resin while a major portion of the gammaglobulin remains unadsorbed and can be recovered from the supernatent for therapeutic use. Preferably, this initial separation of gamma globulin is carried out at a pH of about 6. A portion of the adsorbed $\alpha$- and $\beta$- globulins and fibrinogen can then be recovered by adjusting the resin-protein mixture to a pH of about 4.7 and collecting the desorbed supernatent.

The resin-protein mixture can then be adjusted to a pH range of from about 5.0 to about 5.5 and heated at a temperature of from about 65° C to about 72° C for about one to about four hours. Preferably, the pH is adjusted to about 5.2–5.3 and the resin-protein mixture is heated at about 70° C for about 1 hour.

During the heat treatment step, the residual globulins, principally the $\alpha$- and $\beta$- globulins, are denatured while at the same time the albumin is not denatured and is readily recoverable.

Following the heat treatment, the pH is adjusted to a range of from about 3.5 to about 4.5 to elute the desired albumin from the resin-protein mixture. Preferably, the resin-protein mixture is cooled prior to the pH adjustment and the pH is then adjusted to about 4.

The recovery of the albumin can be carried out by a variety of separation techniques such as sedimentation, filtration, or centrifugation, but preferably by filtration of the pH-adjusted resin-protein mixture, washing of the filter cake and collection of the filtrate as the desired highly purified albumin fraction.

Adjustment of the pH to the desired level during the foregoing processing can be carried out by treatment with acid or alkaline buffer materials known to be clinically acceptable, for example, by the use of sodium acetate-acetic acid buffer or citric acid for acidification or by the use of sodium bicarbonate or sodium hydroxide to increase alkalinity It is also preferable to include known albumin stabilizers such as sodium acetyl tryptophanate and sodium caprylate in the resin-protein mixture during the heat treatment step for their known stabilizing properties.

The following examples will further illustrate the invention although it will be appreciated that the invention is not limited to these specific examples.

EXAMPLE 1

In this example, the polyelectrolyte polymer consisted of the resinous reaction product of substantially equimolar parts of ethylene and maleic anhydride (EMA) cross-linked with methyliminobispropylamine (MIBPA) and then further reacted with dimethylaminopropylamine (DMAPA) such as to provide about five MIBPA cross-linking groups and about 90 DMAPA pendant groups per 100 maleic anhydride units in the EMA copolymer and converted to the HCl salt form. Initially, the polyelectrolyte copolymer was washed in 0.04 molar NaCl. Plasma obtained from pooled human blood was diluted with three parts of water to one part of plasma and then admixed with 2% by weig of the washed polyelectrolyte copolymer (2g/100 ml). The resin plasma mixture was adjusted to a pH of 6.0, mixed for 30 minute filtered and then washed with 0.002 molar NaCl. The filtrate, which consisted of predominantly gamma globulins, beta globulin fibrinogen and associated blood factors, was separated from the remaining resin-protein filter cake. The resin-protein filter cake, which contained the adsorbed albumin, was acidified to a pH of 5.2. Sufficient sodium caprylate stabilizer was admixe with the resin-adsorbed protein to provide a 0.012 molar concentration and NaCl was added to give a 0.002 molar concentration. Heating of the resin-adsorbed protein was then carried out at 70° C for 1 hour, after which time the material was filtered and the filtrate was discarded. The albumin was eluted from the remaining resin-protein filter cake by acidifying to pH 4.0 in 0.002 molar NaCl with citric acid, mixing for 30 minutes, and filtering. The filtrate was retained as the desired albumin fraction in a yield of 96.6% (basis: concentration of albumin in original plasma) and a purity of 98.5%. Albumin purity of the product eluted from the resin was determined by agarose gel electrophoresis in barbital buffer at pH 8.6 with a Corning ACI electrophoresis apparatus. In this determination a Coomassie Brilliant Blue R250 (C.I. 42660) staining procedure was used substantially in accordance with the procedure described by Fazekas de St. Groth et al., *Biochim. Biophys. Acta* 71, 377–91 (1963), and the readings were made with a Gelman ACD-15 densitometer at 600 nm. Coomassie Brilliant Blue R250 is a protein stain of great sensitivity which follows Beer's law up to 20 $\mu$g/cm of width and is sensitive down to 0.5 $\mu$g/cm of width. As a result of this sensitivity, Coomassie Brilliant Blue R250 enables the detection of protein contaminants in the albumin product to a high degree and the stated assay confirms the preparation of an albumin product of high purity.

EXAMPLE 2

The procedure of Example 1 was repeated except that the starting plasma was an AHF-depleted plasma. The yield and purity of the albumin product was substantially similar to that obtained in Example 1.

EXAMPLE 3

The procedure of Example 1 was repeated except that an intermediate step was carried out after the first filtratio prior to the heat treatment step in order to remove additional globulins and fibrinogen from the plasma. In this intermediate step, the resin-protein filter cake from the first filtration was adjusted to pH 4.7 in 0.002 molar NaCl with citric acid and mixed for 30 minutes. The mixture was filtere washed and then subjected to the heat treatment and subsequent steps of Example 1. The filtrate from the treatment at pH 4.7 contained alpha and beta globulins and fibrinogen which can be retained for various known therapeutic or diagnostic uses. The final albumin product was obtained in a yield and purity substantially similar to that of Example 1.

Following the recovery of the purified albumin product in accordance with this invention, the albumin can be concentrated to a desired level and the concentrated product can be adjusted to a physiologically acceptable pH and electrolyte content, further heated to destroy virus, and clarified by filtration or other such procedures to provide a clinically acceptable product and otherwise meet the Bureau of Biologics requirements for a normal serum albumin product. Examples of useful concentration procedures which have been used are (1) lyophilization followed by redissolution to a desired level such as 5% or 25% and (2) ultrafiltration.

Various other examples will be apparent to the person skilled in the art after reading the foregoing specification without departing from the spirit and scope of the invention and it is intended that all such examples be included within the scope of the appended claims.

What is claimed is:

1. A method for the production of a serum albumin fraction in high yield and purity from admixture with other blood protein components comprising contacting the albumin-protein mixture with a resinous polymeric material selected from the group consisting of water-insoluble cross-linked polyelectrolyte copolymers of ethylene and maleic anhydride containing pendant dimethylaminopropyl functional groups at a pH of from about 5.0 to about 5.5 and at a temperature of from about 65° C to about 72° C for about 1 to about 4 hours and then adjusting the mixture to a pH of from about 3.5 to about 4.5 to selectively elute the desired albumin therefrom.

2. The method of claim 1 in which the resinous polymeric material is used in a concentration of from about 1 to about 5% by weight of the albumin-protein mixture.

3. The method of claim 1 in which the resinous polymeric material is cross-linked with methyliminobispropylamine.

4. The method of claim 3 in which the resinous polymeric material contains about five methyliminobispropylamine cross-linking groups and about 90 dimethylaminopropyl pendant groups per 100 maleic anhydride units.

5. The method of claim 1 in which the pH during the heat treatment step is from about 5.2 to about 5.3.

6. The method of claim 1 in which the pH during the elution step is about 4.0.

7. The method of claim 1 in which the heat treatment is carried out at a temperature of about 70° C.

8. The method of claim 1 in which the albumin-protein mixture is whole blood plasma.

9. The method of claim 1 in which the albumin-protein mixture is an AHF-depleted blood plasma fraction.

10. The method of claim 1 in which the albumin-protein mixture is blood plasma which has been fractionated initially to remove gamma globulin.

11. The method of claim 10 in which the initial fractionation to remove gamma globulin comprises contacting the albumin-protein mixture with the resinous polymeric material at a pH of from about 5.5 to about 7.5 and separating the unadsorbed material therefrom as the gamma globulin fraction.

12. The method of claim 11 in which the initial fractionation is carried out at a pH of about 6.0.

13. The method of claim 10 including the additional step of removing alpha and beta globulins comprising adjusting the adsorbed albumin-protein mixture to a pH of about 4.7 and separating the desorbed supernatant therefrom.

* * * * *